US00PP20152P2

(12) United States Plant Patent
Dümmen

(10) Patent No.: US PP20,152 P2
(45) Date of Patent: Jul. 7, 2009

(54) ***VERBENA* PLANT NAMED 'DUEMPDARED'**

(50) Latin Name: *Verbena hybrida*
Varietal Denomination: Duempdared

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/157,320

(22) Filed: Jun. 9, 2008

(51) Int. Cl.
*A01H 5/00* (2006.01)

(52) U.S. Cl. ..... Plt./306

(58) Field of Classification Search ..... Plt./306
See application file for complete search history.

(56) References Cited

PUBLICATIONS

Upov Plant VAriety Database May 2008 PBR for cultivar Duempdared. p. 1.*

* cited by examiner

*Primary Examiner*—Annette H Para
(74) *Attorney, Agent, or Firm*—C. A. Whealy

(57) ABSTRACT

A new and distinct cultivar of *Verbena* plant named 'Duempdared', characterized by its compact, mounding and cascading plant habit; freely branching habit; freely flowering habit; and large dark red-colored flowers that are held above and beyond the foliage in mounded umbels.

1 Drawing Sheet

Botanical designation: *Verbena hybrida.*
Cultivar denomination: 'Duempdared'.

BACKGROUND OF THE INVENTION

The present invention relates to a new and distinct cultivar of *Verbena,* botanically known as *Verbena hybrida,* and hereinafter referred to by the name 'Duempdared'.

The new *Verbena* is a product of a planned breeding program conducted by the Inventor in Rheinberg, Germany. The objective of the breeding program is to create new uniform *Verbena* cultivars with large and attractive flowers.

The new *Verbena* originated from a cross-pollination made by the Inventor in May, 2002 in Rheinberg, Germany of a proprietary selection of *Verbena hybrida* identified as code number V00-3814-1, not patented, as the female, or seed, parent with a proprietary selection of *Verbena hybrida* identified as code number F-20-19, not patented, as the male, or pollen, parent. The new *Verbena* was discovered and selected by the Inventor as a single flowering plant within the progeny of the stated cross-pollination in a controlled greenhouse environment in Rheinberg, Germany in May, 2005.

Asexual reproduction of the new *Verbena* by terminal cuttings in a controlled greenhouse environment in Rheinberg, Germany since May, 2005 has shown that the unique features of this new *Verbena* are stable and reproduced true to type in successive generations.

SUMMARY OF THE INVENTION

Plants of the new *Verbena* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Duempdared'. These characteristics in combination distinguish 'Duempdared' as a new and distinct cultivar of *Verbena:*

1. Compact, mounding and cascading plant habit.
2. Freely branching habit.
3. Freely flowering habit.
4. Large dark red-colored flowers that are held above and beyond the foliage in mounded umbels.

Plants of the new *Verbena* differ from plants of the female parent selection in the following characteristics:

1. Plants of the new *Verbena* are more freely branching than plants of the female parent selection.
2. Plants of the new *Verbena* and the female parent selection differ in flower color as plants of the female parent selection have purple-colored flowers.

Plants of the new *Verbena* differ from plants of the male parent selection in the following characteristics:

1. Plants of the new *Verbena* have larger leaves than plants of the male parent selection.
2. Plants of the new *Verbena* have larger flowers than plants of the male parent selection.

Plants of the new *Verbena* can be compared to plants of the *Verbena hybrida* 'Sunmaribisu', disclosed in U.S. Plant Pat. No. 11,113. In side-by-side comparisons conducted in Rheinberg, Germany, plants of the new *Verbena* differed from plants of 'Sunmaribisu' in the following characteristics:

1. Plants of the new *Verbena* were larger and had longer internodes than plants of 'Sunmaribisu'.
2. Plants of the new *Verbena* had larger leaves than plants of 'Sunmaribisu'.
3. Plants of the new *Verbena* were more freely flowering than plants of 'Sunmaribisu'.
4. Plants of the new *Verbena* had larger inflorescences and flowers than plants of 'Sunmaribisu'.
5. Plants of the new *Verbena* had longer peduncles than plants of the cultivar 'Sunmaribisu'.

BRIEF DESCRIPTION OF THE PHOTOGRAPH

The accompanying colored photograph illustrates the overall appearance of the new *Verbena,* showing the colors as true as it is reasonably possible to obtain in colored reproductions of this type. Colors in the photograph may differ slightly from the color values cited in the detailed botanical description which accurately describe the colors of the new *Verbena*. The photograph comprises a close-up view of typical leaves and flowers of 'Duempdared'.

DETAILED BOTANICAL DESCRIPTION

The aforementioned photographs and following observations, measurements and values describe plants grown 13-cm containers in Rheinberg, Germany in a glass-covered greenhouse during the spring and under conditions which closely approximate commercial production. During the production of the plants, day and night temperatures averaged 18° C. and light levels averaged 4,500 lux. Plants were pinched one time about one week after planting. Plants were four months old when the photograph and the description were taken. In the description, color references are made to The Royal Horticultural Society Colour Chart, 1995 Edition, except where general terms of ordinary dictionary significance are used.

Botanical classification: *Verbena hybrida* 'Duempdared'.

Parentage:

*Female, or seed, parent.*—Proprietary selection of *Verbena hybrida* identified as code number V00-3814-1, not patented.

*Male, or pollen, parent.*—Proprietary selection of *Verbena hybrida* identified as code number F-20-19, not patented.

Propagation:

*Type.*—Terminal cuttings.

*Time to initiate roots, summer and winter.*—About ten days at 20° C.

*Time to produce a rooted cutting, summer.*—About 21 days at 20° C.

*Time to produce a rooted cutting, winter.*—About 25 days at 20° C.

*Root description.*—Fine, fibrous; white in color.

*Rooting habit.*—Freely branching; dense.

Plant description:

*Plant habit.*—Initially upright, then mounding to cascading plant habit; compact growth habit. Freely branching habit with about four to six primary lateral branches with secondary lateral branches potentially forming at every node; pinching enhances lateral branch development; dense and bushy plant habit. Moderately vigorous growth habit.

*Plant height.*—About 15 cm.

*Plant diameter.*—About 20 cm.

Lateral branch description:

*Length.*—About 18 cm.

*Diameter.*—About 3 mm.

*Internode length.*—About 5.5 cm.

*Texture.*—Pubescent.

*Color.*—Close to 144A.

Foliage description:

*Arrangement.*—Opposite, simple.

*Length.*—About 5.2 cm.

*Width.*—About 3.6 cm.

*Shape.*—Lanceolate, deeply dissected; doubly pinnatifid.

*Apex.*—Acute.

*Base.*—Attenuate.

*Margin.*—Deeply dissected.

*Texture, upper and lower surfaces.*—Pubescent, coarse.

*Venation pattern.*—Pinnate.

*Color.*—Developing and fully expanded foliage, upper surface: Close to 146A; venation, close to 146D. Developing and fully expanded foliage, lower surface: Close to 146B; venation, close to 146D.

*Petiole length.*—About 9.2 mm.

*Petiole diameter.*—About 3.4 mm.

*Petiole texture, upper and lower surfaces.*—Smooth, pubescent.

*Petiole color, upper surface.*—Close to 146A.

*Petiole color, lower surface.*—Close to 146B.

Flower description:

*Flower arrangement and habit.*—Salverform flowers arranged in hemispherical terminal umbels; umbels dense and mounding; numerous umbels covering the entire plant. Flowers face upward or outward. Freely flowering habit with about 60 flowers and flower buds per inflorescence. Flowers not fragrant.

*Natural flowering season.*—Plants flower continuously from the spring through the fall in Germany. Plants begin flowering about eight weeks after planting.

*Flower longevity.*—Individual flowers last about one week on the plant. Flowers persistent.

*Inflorescence size.*—Height: About 5 cm. Diameter: About 6.5 cm.

*Flowers.*—Appearance: Flared trumpet, corolla fused, five-parted. Diameter: About 2.1 cm. Depth: About 3 cm.

*Flower buds.*—Length: About 1.4 cm. Diameter: About 3 mm. Shape: Oval, tubular. Color: Close to 146A.

*Corolla.*—Arrangement: Single whorl of five fused petals. Petal lobe length: About 3.4 cm. Petal lobe width: About 1.2 cm. Petal lobe shape: Obovate. Petal lobe apex: Emarginate to cordate. Petal margin: Entire. Petal texture, upper and lower surfaces: Smooth, glabrous; velvety. Color: Petal, when opening and fully opened, upper surface: Close to 45B: color becoming closer to 45D with development. Petal, when opening and fully opened, lower surface: Close to 45D.

*Calyx.*—Arrangement: Star-shaped calyx with five fused sepals. Sepal length: About 1.2 cm. Sepal width: About 1 mm. Sepal shape: Ligulate. Sepal apex: Acute. Sepal margin: Entire. Sepal texture, upper and lower surfaces: Pubescent, coarse. Sepal color, upper and lower surfaces: Between 146D and 144A.

*Peduncles.*—Length: About 8.1 cm. Diameter: About 2 mm. Strength: Strong. Texture: Pubescent. Color: Close to 144A.

*Pedicels.*—Length: About 0.5 mm. Diameter: About 0.5 mm. Strength: Strong. Texture: Smooth, glabrous. Color: Close to 144A.

*Reproductive organs.*—Stamens: Quantity/arrangement: About four to five per flower, adnate to corolla tube. Anther shape: Oval. Anther length: About 0.75 mm. Anther color: Close to 144B. Pollen amount: Moderate. Pollen color: Close to 2D. Pistils: Quantity: One per flower. Pistil length: About 1.9 cm. Stigma shape: Bi-parted. Stigma color: Close to 144A. Style length: About 1.7 cm. Style color: Close to 144D. Ovary color: Close to 144C.

*Fruits/seeds.*—Fruit and seed development has not been observed.

Temperature tolerance: Plants of the new *Verbena* have been observed to tolerate temperatures from about 5° C. to about 35° C.

Pathogen/pest resistance: Plants of the new *Verbena* have not been observed to be resistant to pathogens and pests common to *Verbenas*.

It is claimed:

1. A new and distinct *Verbena* plant named 'Duempdared' as illustrated and described.

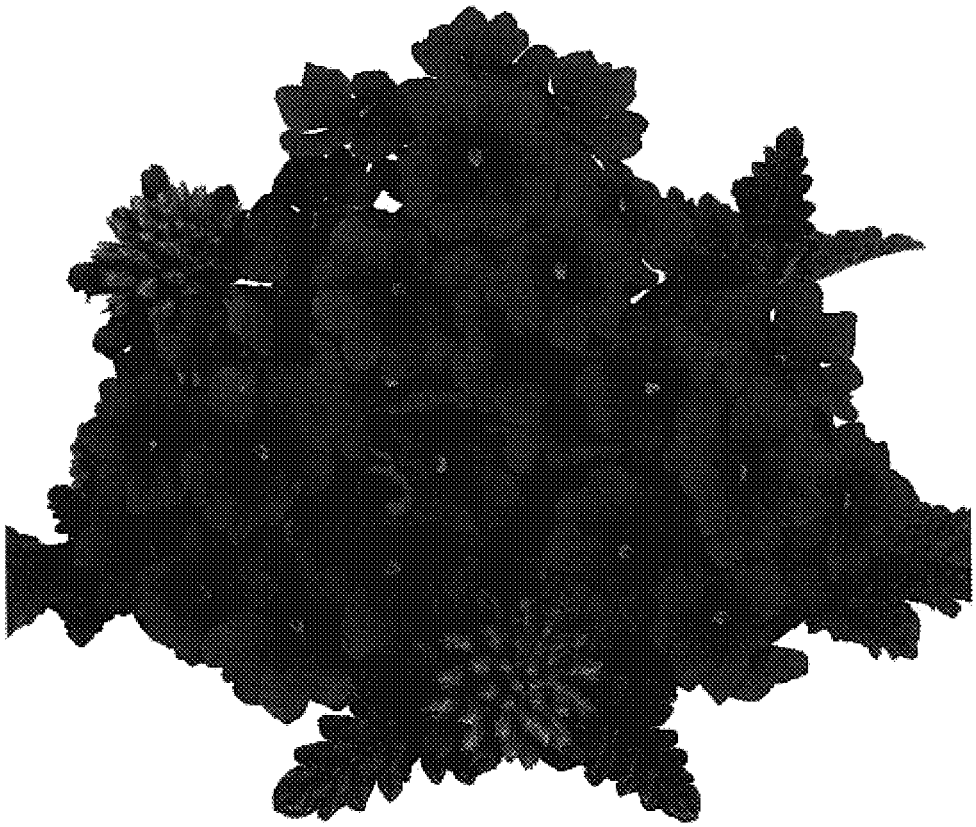

* * * * *